United States Patent
Xavier et al.

(10) Patent No.: US 10,039,939 B2
(45) Date of Patent: Aug. 7, 2018

(54) SULFATE-FREE CLEANSING COMPOSITION WITH THICKENER

(71) Applicant: L'OREAL, Paris (FR)

(72) Inventors: Liliana Santos Xavier, Elizabeth, NJ (US); Kirolos Kamal Rizk, Helmetta, NJ (US); Eva Eliza Zion, Bridgewater, NJ (US)

(73) Assignee: L'OREAL, Paris (FR)

( * ) Notice: Subject to any disclaimer, the term of this patent is extended or adjusted under 35 U.S.C. 154(b) by 386 days.

(21) Appl. No.: 14/503,470

(22) Filed: Oct. 1, 2014

(65) Prior Publication Data

US 2016/0095804 A1 Apr. 7, 2016

(51) Int. Cl.
*A61K 8/44* (2006.01)
*A61Q 5/12* (2006.01)
*A61Q 5/02* (2006.01)
*A61K 8/81* (2006.01)

(52) U.S. Cl.
CPC ............... *A61Q 5/12* (2013.01); *A61K 8/44* (2013.01); *A61K 8/8152* (2013.01); *A61Q 5/02* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 5,490,955 A * | 2/1996 | Hagan | A61K 8/37 424/70.19 |
| 6,894,012 B2 * | 5/2005 | Sebillotte-Arnaud | A61K 8/25 510/119 |
| 2006/0217283 A1 | 9/2006 | De Salvert et al. | |
| 2012/0213725 A1 * | 8/2012 | Galleguillos | A61K 8/463 424/70.16 |
| 2012/0308492 A1 | 12/2012 | Allef et al. | |
| 2013/0136709 A1 | 5/2013 | Pillai et al. | |

FOREIGN PATENT DOCUMENTS

| | | | |
|---|---|---|---|
| EP | 2216226 | * | 11/2009 |
| WO | 2010/121876 A1 | | 10/2010 |
| WO | 2011/130460 A1 | | 10/2011 |
| WO | 2013/092719 A1 | | 6/2013 |

OTHER PUBLICATIONS

Lubrizol Advanced Material Inc; NovethixTM L-10 Polymer; Technical Data Sheet TDS-752; Dec. 13, 2012; www.lubrizol.com/personalcare.

Lubrizol Advanced Material Inc; Mild and Gentle Sulfte Free Shampoo; SH-0057; May 4, 2012; Reference# NO1460-012-08-092 (JEMUL); www.lubrizol.com/personalcare.

Lubrizol Advanced Material Inc; Measurement and Understanding of Yield Value in Personal Care Formulations; Technical Data Sheet TDS-244; Oct. 15, 2007; www.lubrizol.com/personalcare .

Joel Basilan, Denise Beitia; Innovative Solutions for Hair Color Maintenance; downloaded Jun. 26, 2014; http://www.happi.com/contents/view_features/2008-12-01/innovative-solutions-for-hair-color-maintenan/.

Eclat & soin couleur de l'Occitane; downloaded May 15, 2014; http://oh-vintage.eklablog.com/eclat-soin-couleur-de-l-occitane-a60375711 .

Liquid Detergents (Surfactant Science); Surfactant Science (Book 129); CRC Press, 2 Edition, Aug. 23, 2005; ISBN-10: 1420054112; ISBN-13: 978-0824758356; ASIN: 0824758358; downloaded Aug. 22, 2014; http://www.amazon.com/Liquid-Detergents-Surfactant-Science-Kuo-Yann/dp/0824758358.

* cited by examiner

Primary Examiner — Necholus Ogden, Jr.
(74) Attorney, Agent, or Firm — Maria Luisa Balasta

(57) ABSTRACT

Disclosed is an aqueous cleansing composition comprising (a) at least one anionic surfactant that is not an alkyl sulfate or alkyl ether sulfate, (b) at least one amphoteric surfactant, (c) at least one thickener selected from a hydrophobically-modified acrylic acid based copolymer having a molecular weight from about 80,000 to about 2,500,000 grams per mole, (d) at least one cationic conditioning agent, and (e) optionally at least one nonionic surfactant; wherein the ratio of the anionic surfactant (a) to amphoteric surfactant (b) is less than about 9.5, by weight. Also disclosed are methods of cleaning and conditioning hair using said compositions and methods of making said compositions.

17 Claims, No Drawings

SULFATE-FREE CLEANSING COMPOSITION WITH THICKENER

TECHNICAL FIELD

The present invention relates to personal cleansing compositions. More particularly, the invention relates to a sulfate-free cleansing composition, for example a shampoo, having improved conditioning properties.

BACKGROUND OF THE INVENTION

Conventional cleansing compositions such as shampoos, for example, contain standard surfactants such as anionic, nonionic and/or amphoteric type surfactants.

These cleaning compositions can be applied onto a wet keratinous substrate (e.g. hair or skin) and the lather they generate make it possible, after rinsing with water, to remove the diverse types of soils typically present on the hair or skin.

While these compositions provide good cleansing power, they often have poor intrinsic cosmetic properties due to the fact that the relatively aggressive nature of such a cleansing treatment may, in the long term, give rise to more or less pronounced damage on hair fibers or skin associated, for example, with the gradual removal of the fats or proteins contained in or at their surface. Thus, to improve the cosmetic properties of cleansing compositions, cationic compounds are sometimes added to such compositions to act as conditioning agents and improve the tactile properties of said compositions.

As described above, typical cleansing compositions, in particular shampoos, include a number of active surfactants to effect both cleansing and conditioning. The use of increased types and amounts of surfactants increases the cost of the resulting compositions.

Consumers prefer sulfate-free cleansing compositions due to perceived mildness and desirable sensorial experience. However, sulfate-free cleansers are difficult to thicken sufficiently to afford the user good usage qualities. Currently two approaches are leveraged to attempt to thicken such formulas. One approach is to use high levels of surfactants to benefit from the self-assembling properties of such ingredients. This approach is most common but it is also costly. The second approach is to use high levels of rheology modifiers which can adversely impact the properties of the composition such as by decreasing the foam and ease of distribution of the composition.

Aqueous cleansing compositions are desirable as being more environmentally friendly as well as safer for consumers. However, aqueous compositions can be thin and runny making them undesirable for personal use. Thickeners, including rheology modifiers, can be used to increase the viscosity of such compositions making them more aesthetically pleasing. The use of surfactant-polymer blends to increase the viscosity of cleansing compositions is described, for example, in US2012/0213725. However, as mentioned above, use of such viscosity increasing thickeners can adversely affect both the cleansing and/or foaming properties of cleansing composition requiring the use of increased amounts of the cleansing surfactants.

Thus, there remains a need for a cleansing composition, particularly a shampoo, which is effective at cleaning even while containing lower amount of active surfactants than typical cleansing products, but also still possesses good esthetic properties such as good foam, and is thick and creamy in texture, is silky to the touch and affords conditioning.

BRIEF SUMMARY OF THE INVENTION

The present invention relates to an aqueous cleansing composition comprising:
(a) from about 3% to about 14%, by weight, of at least one anionic surfactant that is not an alkyl sulfate or alkyl ether sulfate;
(b) from about 0.5% to about 8%, by weight, of at least one amphoteric surfactant;
(c) from about 0.01% to about 2.0%, by weight, of a thickener selected from a hydrophobically-modified acrylic acid based copolymer having a molecular weight from about 80,000 to about 2,500,000 grams per mole;
(d) from about 0.01% to about 2%, by weight, of at least one cationic conditioning agent; and
(e) optionally at least one nonionic surfactant;
wherein the ratio of the sum of anionic surfactant (a), amphoteric surfactant (b) and nonionic surfactant (e) to viscosity increasing agent (c), by weight, is from about 1 to about 800; the ratio of the anionic surfactant (a) to amphoteric surfactant (b) is less than about 9.5, by weight; all weights and ratios being based on the weight percent of each component in the final composition.

The present invention is also directed to a process for cleansing a keratinous substrate involving contacting the keratinous substrate with the above-disclosed composition.

The present invention is also directed to a method of cleansing and conditioning a keratinous substrate involving contacting the keratinous substrate with the above-disclosed composition.

The present invention is also directed to a method of increasing the deposition of cationic conditioning agents onto a keratinous substrate involving contacting the keratinous substrate with the composition of the invention.

The present invention is also directed to a process for making an aqueous cleansing composition comprising contacting:
(a) from about 3% to about 14%, by weight, of at least one anionic surfactant that is not an alkyl sulfate or alkyl ether sulfate;
(b) from about 0.5% to about 8%, by weight, of at least one amphoteric surfactant;
(c) from about 0.01% to about 2.0%, by weight, of a thickener selected from a hydrophobically-modified acrylic acid based copolymer having a molecular weight from about 80,000 to about 2,500,000 grams per mole;
(d) from about 0.01% to about 2%, by weight, of at least one cationic conditioning agent; and
(e) optionally at least one nonionic surfactant;
wherein the ratio of the sum of anionic surfactant (a), amphoteric surfactant (b) and nonionic surfactant (e) to viscosity increasing agent (c), by weight, is from about 1 to about 800; the ratio of the anionic surfactant (a) to amphoteric surfactant (b) is less than about 9.5, by weight; all weights and ratios being based on the weight percent of each component in the final composition.

It is to be understood that both the foregoing general description and the following detailed description are exemplary and explanatory only, and are not restrictive of the invention.

DETAILED DESCRIPTION OF THE INVENTION

The compositions of the invention provide not only good cleansing of keratinous substrates with reduced amounts of surfactant(s), but also create good and luxuriously feeling foam, while at the same time imparting increased conditioning properties onto the substrate. The compositions of the invention remain stable even at elevated (e.g. 45° C.) or reduced temperatures (e.g. 4° C.).

The use of a thickener selected from a hydrophobically-modified acrylic acid based copolymer having a molecular weight from about 80,000 to about 2,500,000 grams per mole in the instant sulfate-free cleansing composition advantageously increases the viscosity of the composition without weighing down the substrate, such as hair.

All percentages and ratios are calculated by weight unless otherwise indicated. All percentages are calculated based on the weight of the total composition unless otherwise indicated.

As used herein, all ranges provided are meant to include every specific range within, and combination of sub ranges between, the given ranges. Thus, a range from 1 to 5, includes 1, 2, 3, 4, and 5 as well as 1-4, 2-4, 1-3, etc.

Definitions

"About" as used herein means within 10% of the indicated number (e.g. "about 10%" means 9%-11% and "about 2%" means 1.8%-2.2%).

"At least one" as used herein means one or more and thus includes individual components as well as mixtures/combinations.

"Comprising" as used herein is used in the inclusive sense of "having" or "including" and not in the exclusive sense of "consisting only of."

"Conditioning" as used herein means imparting to hair at least one property chosen from compatibility, manageability, moisture-retentivity, luster, shine, and softness. The state of conditioning is evaluated by measuring, and comparing the ease of combing of the treated hair in contrast with the untreated hair.

"Good foam" means that the foam produced is in high quantity and is stable and creamy over the period of use.

"HLB" as used herein means the hydrophilic-lipophilic balance of a molecule. It is the ratio between the hydrophilic part and lipophilic part of a molecule. This term is well known to those skilled in the art. See, e.g., "The HLB System: A Time-saving Guide to Emulsifier Selection" (Pub: ICI Americas Inc., 1984) and US2006/0217283 at [0053], both of which, to the extent required, are herein incorporated by reference.

"INCI" is an abbreviation of International Nomenclature of Cosmetic Ingredients, which is a system of names provided by the International Nomenclature Committee of the Personal Care Products Council to describe personal care ingredients. "Keratinous substrates", as used herein, include but are not limited to, skin, hair, lips, eyelashes and nails. A Preferred keratinous substrate is hair.

The present invention relates to an aqueous cleansing composition comprising:
  (a) from about 3% to about 14%, by weight, of at least one anionic surfactant that is not an alkyl sulfate or alkyl ether sulfate;
  (b) from about 0.5% to about 8%, by weight, of at least one amphoteric surfactant;
  (c) from about 0.01% to about 2.0%, by weight, of a thickener selected from a hydrophobically-modified acrylic acid based copolymer having a molecular weight from about 80,000 to about 2,500,000 grams per mole;
  (d) from about 0.01% to about 2%, by weight, of at least one cationic conditioning agent; and
  (e) optionally at least one nonionic surfactant;
  wherein the ratio of the sum of anionic surfactant (a), amphoteric surfactant (b) and nonionic surfactant (e) to viscosity increasing agent (c), by weight, is from about 10 to about 800; the ratio of the anionic surfactant (a) to amphoteric surfactant (b) is less than about 9.5, by weight; all weights and ratios being based on the weight percent of each component in the final composition.

In another embodiment, the invention relates to a method of cleansing and conditioning a keratinous substrate comprising contacting said substrate with an aqueous cleansing composition comprising:
  (a) from about 3% to about 14%, by weight, of at least one anionic surfactant that is not an alkyl sulfate or alkyl ether sulfate;
  (b) from about 0.5% to about 8%, by weight, of at least one amphoteric surfactant;
  (c) from about 0.01% to about 2.0%, by weight, of a thickener selected from a hydrophobically-modified acrylic acid based copolymer having a molecular weight from about 80,000 to about 2,500,000 grams per mole;
  (d) from about 0.01% to about 2%, by weight, of at least one cationic conditioning agent; and
  (e) optionally at least one nonionic surfactant;
  wherein the ratio of the sum of anionic surfactant (a), amphoteric surfactant (b) and nonionic surfactant (e) to viscosity increasing agent (c), by weight, is from about 1 to about 800; the ratio of the anionic surfactant (a) to amphoteric surfactant (b) is less than about 9.5, by weight; all weights and ratios being based on the weight percent of each component in the final composition.

In another embodiment the present invention is directed to a process for making an aqueous cleansing composition comprising contacting:
  (a) from about 3% to about 14%, by weight, of at least one anionic surfactant that is not an alkyl sulfate or alkyl ether sulfate;
  (b) from about 0.5% to about 8%, by weight, of at least one amphoteric surfactant;
  (c) from about 0.01% to about 2.0%, by weight, of a thickener selected from a hydrophobically-modified acrylic acid based copolymer having a molecular weight from about 80,000 to about 2,500,000 grams per mole;
  (d) from about 0.01% to about 2%, by weight, of at least one cationic conditioning agent; and
  (e) optionally at least one nonionic surfactant;
  wherein the ratio of the sum of anionic surfactant (a), amphoteric surfactant (b) and nonionic surfactant (e) to viscosity increasing agent (c), by weight, is from about 1 to about 800; the ratio of the anionic surfactant (a) to amphoteric surfactant (b) is less than about 9.5, by weight; all weights and ratios being based on the weight percent of each component in the final composition.

In particular embodiments, the ratio of the sum of anionic surfactant (a), amphoteric surfactant (b) and nonionic surfactant (e) to viscosity increasing agent (c), by weight, is from about 1 to about 800, such as from about 5 to about 700, most typically from about 10 to about 600, including all ranges and sub ranges therebetween. Put another way [(a)+(b)+(e)/(c)=from about 1 to about 800].

Additionally, in a particular embodiment, the ratio of at least one anionic surfactant (a) to the at least amphoteric surfactant (b) is greater than 0.1 and less than about 9.

It has been found that the ratio of the at least one anionic surfactant (a) to the at least amphoteric surfactant (b) is important to obtain optimal balance between mildness, foaming, detergency and conditioning of the composition. For example, when the ratio (a):(b) is less than about 0.1 the foaming and detergency of the compositions is reduced. When the ratio is greater than about 9.5 the detergency of the composition also declines. Thus, the ratio of the at least one anionic surfactant (a) to the at least amphoteric surfactant (b) is less than 9.5, such as less than 9. In a particular embodiment, the ratio (a):(b) is greater than about 0.1 and less than about 9.5, particularly from about 0.7 to about 9, more particularly from about 1 to about 8, even more particularly from about 1.2 to about 7, most particularly from about 1.5 to about 5.

In a particular embodiment the keratinous substrate is hair.

Anionic Surfactant (a)

The compositions of the invention include at least one anionic surfactant that is not an alkyl sulfate or alkyl ether sulfate. These surfactants can be chosen from salts, for example, alkali metal salts such as sodium salts, ammonium salts, amine salts, amino alcohol salts and alkaline-earth metal salts. Examples of alkaline-earth metal salts include magnesium salts of the following types of compounds: acyl isethionates, acyl glycinates, acyl taurates, acyl amino acids, acyl sarcosinates, sulfosuccinates, sulfonates, and sulfoacetates, the alkyl and acyl groups of all these compounds comprising from 6 to 24 carbon atoms (saturated or unsaturated, linear or branched).

Non-limiting examples of acyl amino acids useful in the compositions of the invention include those having the following formula:

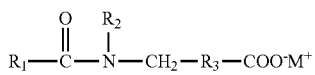

(VIII)

wherein $R^1$, $R^2$ and $R^3$ are each independently selected from H and an alkyl chain that has 1-24 carbon atoms, said chain being saturated or unsaturated, linear or branched; and M is an alkali-metal salt.

Acyl amino acids that can be used in the current compositions include amino acid surfactants based on glycine, sarcosine, threonine, glutamine, glutamic acid or alanine. The most common salt ions attached to the at least one acyl amino acid are sodium or potassium. The salt ion attached to the acyl amino acid can also be an organic salt, such as triethanolamine (TEA), or a metal salt. Examples of acyl amino acid compounds include, but are not limited to, sodium cocoyl glycinate, potassium cocoyl glycinate, sodium lauroyl sarcosinate, sodium cocoyl alaninate, and salts thereof, and mixtures therefor. Typically, the at least one acyl amino acid is selected from the group consisting of sodium cocoyl glycinate, sodium lauroyl sarcosinate (aka sodium N-lauryl sarcosinate), and mixtures thereof.

Non-limiting examples of taurates useful in the compositions of the invention include those having the following formula:

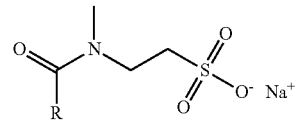

(IX)

wherein R is selected from H or an alkyl chain that has 1-24 carbon atoms, said chain being saturated or unsaturated, linear or branched.

A particular taurate that can be used in the current compositions is sodium methyl cocoyl taurate.

Non-limiting examples of isethionates useful in the compositions of the invention include those having the formulas below:

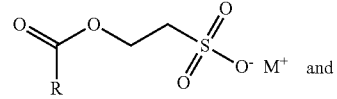

(XA)

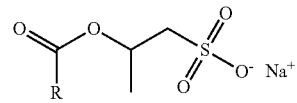

(XB)

wherein R is selected from H or an alkyl chain that has 1-24 carbon atoms, said chain being saturated or unsaturated, linear or branched.

Particular isethionates that can be used in the current compositions include, for example, sodium cocoyl isethionate, sodium lauroyl methyl isethionate, and mixtures thereof.

Non-limiting examples of sulfosuccinates useful in the compositions of the invention include those having the following formula:

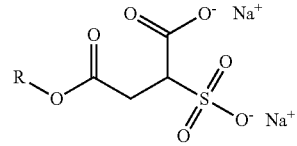

(XI)

wherein R is selected from H or an alkyl chain that has 1-24 carbon atoms, said chain being saturated or unsaturated, linear or branched.

A particular sulfosuccinate that can be used in the current compositions is disodium laureth sulfosuccinate.

Non-limiting examples of sulfonates useful in the compositions of the invention include those having the following formula:

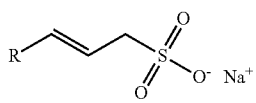
(XII)

wherein R is selected from H or an alkyl chain that has 1-24 carbon atoms, said chain being saturated or unsaturated, linear or branched.

A particular sulfonate that can be used in the current compositions is sodium C14-16 olefin sulfonate.

Non-limiting examples of sulfoacetates useful in the compositions of the invention include those having the following formula:

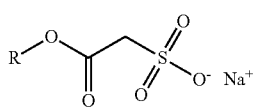
XIII wherein R is as defined above for the sulfonates.

A particular sulfoacetate that can be used in the current compositions is sodium lauryl sulfoacetate.

The at least one anionic surfactant is present in a total amount ranging from about 3% to about 14% by weight, typically from about 4.2% to about 13%, more typically from about 4.5% to about 12% by weight, including all ranges and sub ranges therebetween, based on the total weight of the composition. In an embodiment, the amount of anionic surfactant is from about 5.5% to about 11%.

Amphoteric Surfactant (b)

The compositions of the invention include at least one amphoteric surfactant. Such surfactants are typically selected from betaines, sultaines, amphoacetates, amphoproprionates, and mixtures thereof. More typically, betaines and amphoproprionates are used, and most typically betaines.

Non-limiting examples of betaines which can be used in the current compositions include those having the formulas (IIIA-D) below:

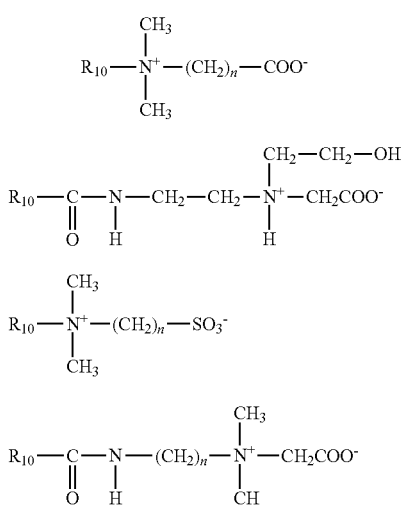

wherein
$R^{10}$ is an alkyl group having 8-18 carbon atoms; and
n is an integer from 1 to 3.

Particularly useful betaines include, for example, coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocamidopropyl betaine, behenyl betaine, capryl/capramidopropyl betaine, lauryl betaine, and mixtures thereof, and more typically coco betaine, cocamidopropyl betaine, and mixtures thereof.

Non-limiting examples of hydroxyl sultaines useful in the compositions of the invention include the following

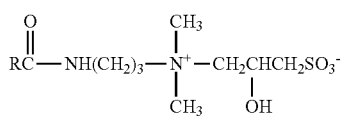
(IV)

wherein
R is an alkyl group having 8-18 carbon atoms.

Non-limiting examples of alkylamphoacetates useful in the instant compositions include those having the formula (V)

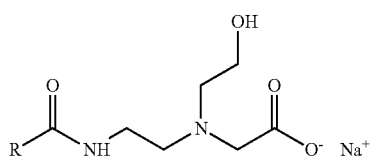
(V)

wherein
R is an alkyl group having 8-18 carbon atoms.

Non-limiting examples of alkyl amphodiacetates useful in the current invention include those having the formula (VI)

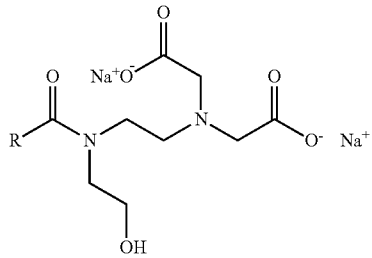
(VI)

wherein
R is an alkyl group having 8-18 carbon atoms.

In the present compositions, the at least one amphoteric surfactant (b) is used in an amount of from about 0.5% to about 8% by weight, typically from about 0.75% to about 7% by weight, and more typically from about 1% to about 6% by weight, including all ranges and sub ranges therebetween, based on the total weight of the composition as a whole. In an embodiment the amphoteric surfactant is used in an amount of from about 2% to about 5%, by weight.

Hydrophobically-Modified Polymer Thickener (c)

The compositions of the present invention comprise at least one thickener selected from a hydrophobically-modified acrylic acid based copolymer having a molecular weight from about 80,000 to about 2,500,000 grams.

The hydrophobically-modified acrylic acid based copolymer thickeners useful in the invention compositions are different from "suspending agents" at least in that suspending agents have greater yield stress which enables the stable entrapment of insoluble particle in such suspending agents. In contrast, when used alone, thickeners such as those used herein, typically are not capable of entrapping/suspending insoluble particles such as to create a stable suspension. See, e.g., Technical Data Sheet TDS-244 (Lubrizol Advanced Materials; January, 2002; https://www.lubrizol.com/home-care/documents/technical-data-sheets/tds-244-measure-ment-understanding-yield-value-personal-care-formulations.pdf).

In certain exemplary and non-limiting embodiments, the thickening copolymers are chosen from the copolymers resulting from the polymerization of: at least one monomer of formula (II):

$$CH_2=CH(R_1)COOH \quad (II)$$

wherein $R_1$ is chosen from H or $CH_3$ or $C_2H_5$, providing acrylic acid, methacrylic acid, or ethacrylic acid monomers, and at least one monomer of $(C_{10}-C_{30})$alkyl ester of unsaturated carboxylic acid type corresponding to the monomer of formula (III):

$$CH_2=CH(R_2)COOR_3 \quad (III)$$

wherein $R_2$ is chosen from H or $CH_3$ or $C_2H_5$, providing acrylate, methacrylate or ethacrylate units, $R_3$ denoting a $C_{10}-C_{30}$ alkyl radical, such as a $C_{12}-C_{22}$ alkyl radical.

Non-limiting examples of $(C_{10}-C_{30})$alkyl esters of unsaturated carboxylic acids are for example chosen from lauryl acrylate, stearyl acrylate, decyl acrylate, isodecyl acrylate, dodecyl acrylate and the corresponding methacrylates, such as lauryl methacrylate, stearyl methacrylate, decyl methacrylate, isodecyl methacrylate and dodecyl methacrylate, and mixtures thereof.

Additionally, crosslinked thickening polymers may be chosen according to further exemplary embodiments. For example, such polymers may be chosen from polymers resulting from the polymerization of a mixture of monomers comprising:
  acrylic acid,
  an ester of formula (III) described above, in which $R_2$ is chosen from H or $CH_3$, $R_3$ denoting an alkyl radical having from 12 to 22 carbon atoms, and
  a crosslinking agent, which is a well-known copolymerizable polyethylenic unsaturated monomer, such as diallyl phthalate, allyl (meth)acrylate, divinylbenzene, (poly)ethylene glycol dimethacrylate and methylenebisacrylamide.

By way of example, crosslinked thickening polymers comprising about 60% to about 95% by weight of acrylic acid (hydrophilic unit), about 4% to about 40% by weight of $C_{10}-C_{30}$ alkyl acrylate (hydrophobic unit), and about 0% to about 6% by weight of crosslinking polymerizable monomer. In yet further embodiments, the crosslinked thickening polymers may comprise about 96% to about 98% by weight of acrylic acid (hydrophilic unit), about 1% to about 4% by weight of $C_{10}-C_{30}$ alkyl acrylate (hydrophobic unit), and about 0.1% to 0.6% by weight of crosslinking polymerizable monomer, such as those described above.

Such copolymers may be selected, for example, from acrylate/$C_{10}-C_{30}$ alkyl acrylate copolymers (INCI name: Acrylates/C10-30 Alkyl Acrylate Crosspolymer), such as the products sold by Lubrizol under the trade names PEMULEN™ TR1, PEMULEN™ TR2, CARBOPOL® 1382 and CARBOPOL® EDT 2020.

In further embodiments, the at least one thickening agent may be chosen from nonionic homopolymers or copolymers containing ethylenically unsaturated monomers of the ester and/or amide type. Examples of such agents include the products sold under the names CYANAMER P250 by the company CYTEC (polyacrylamide), methyl methacrylate/ethylene glycol dimethacrylate copolymers (such as PMMA MBX-8C by the company US COSMETICS), butyl methacrylate/methyl methacrylate copolymers (such as ACRYLOID B66 by the company RHOM HMS), and polymethyl methacrylates (BPA 500 by the company KOBO) may be chosen.

Hydrophilic thickeners, for example cellulose polymers and gums, may also be used. As used herein, the term "hydrophilic thickener" is meant to indicate that the thickening agent is soluble or dispersible in water. Non-limiting examples of hydrophilic thickeners include modified or unmodified carboxyvinyl polymers, such as the products sold under the name CARBOPOL (CTFA name: carbomer) by Goodrich, homopolymers or copolymers of acrylic or methacrylic acids or the salts thereof and the esters thereof, such as the products sold under the names VERSICOL F® or VERSICOL K® by Allied Colloid, ULTRAHOLD 8® by Ciba-Geigy, polyacrylates and polymethacrylates such as the products sold under the names LUBRAJEL and NORGEL by Guardian, or under the name HISPAJEL by Hispano Chimica, and polyacrylic acids of SYNTHALEN K type, polyacrylamides, copolymers of acrylic acid and of acrylamide sold in the form of the sodium salt thereof, such as under the names RETEN® by Hercules, the sodium polymethacrylate such as sold under the name DARVAN 7® by Vanderbilt, and the sodium salts of polyhydroxycarboxylic acids such as sold under the name HYDAGEN F® by Henkel, optionally crosslinked and/or neutralized 2-acrylamido-2-methylpropanesulphonic acid polymers and copolymers, for instance poly(2-acrylamido-2-methylpropanesulphonic acid) such as sold by Clariant under the name HOSTACERIN AMPS (CTFA name: ammonium polyacryldimethyltauramide), crosslinked anionic copolymers of acrylamide and of AMPS, e.g. in the form of a water-in-oil emulsion, such as those sold under the name SEPIGEL™ 305 (CTFA name: Polyacrylamide/C13-14 Isoparaffin/Laureth-7) and under the name SIMULGEL™ 600 (CTFA name: Acrylamide/Sodium acryloyldimethyltaurate copolymer/Isohexadecane/Polysorbate 80) by SEPPIC, polyacrylic acid/alkyl acrylate copolymers of PEMULEN type, associative polymers, for instance PEG-150/stearyl alcohol/SMDI copolymer such as sold under the name ACULYN™ 46 by Rohm & Haas, steareth-100/PEG-136/HDI copolymer such as sold under the name RHEOLATE® FX 1100 by Elementis), as well as mixtures thereof.

In a particular embodiment, the thickener is selected from acrylates/beheneth-25 methacrylate copolymers, such as the product NOVETHIX® L-10 sold by Lubrizol.

In the present compositions, the at least one thickener selected from a hydrophobically-modified acrylic acid based copolymer is used in an amount of from about 0.01% to about 2% by weight, typically from about 0.05% to about 1.5% by weight, and more typically from about 0.1% to about 1% by weight, including all ranges and sub ranges therebetween, based on the total weight of the composition as a whole.

Additional Thickener (Optional)

In an embodiment, the compositions of the invention optionally may include an additional thickener different from the hydrophobically-modified acrylic acid based copolymer thickener. This second thickener may be selected from, for example, associative polymers. As used herein, the term "associative polymer" is intended to mean any amphiphilic polymer comprising in its structure at least one fatty chain and at least one hydrophilic portion. The associative polymers in accordance various exemplary embodiments may be anionic, cationic, nonionic or amphoteric. By way of example, associative polymers which may be chosen include those comprising at least one hydrophilic unit and at least one fatty-chain allyl ether unit, such as those in which the hydrophilic unit is constituted of an ethylenic unsaturated anionic monomer, such as a vinylcarboxylic acid or an acrylic acid, a methacrylic acid, and mixtures thereof, and in which the fatty-chain allyl ether unit corresponds to the monomer of formula (I) below:

$$CH_2=C(R')CH_2OB_nR \quad (I)$$

in which R' is chosen from H or $CH_3$, B is chosen from an ethyleneoxy radical, n is zero or is chosen from an integer ranging from 1 to 100, and R is chosen from a hydrocarbon-based radical chosen from alkyl, arylalkyl, aryl, alkylaryl and cycloalkyl radicals containing from 8 to 30 carbon atoms, such as from 10 to 24 carbon atoms, or from 12 to 18 carbon atoms. Exemplary and non-limiting polymers of this type are described and prepared, according to an emulsion polymerization process, in patent EP 0 216 479.

Non-limiting examples of associative anionic polymers that may also be chosen include anionic polymers comprising at least one hydrophilic unit of olefinic unsaturated carboxylic acid type, and at least one hydrophobic unit exclusively of $(C_{10}-C_{30})$alkyl ester of unsaturated carboxylic acid type. Examples that may be mentioned include, but are not limited to, the anionic polymers described and prepared according to U.S. Pat. Nos. 3,915,921 and 4,509,949.

Cationic associative polymers that may be chosen include, but are not limited to, quaternized cellulose derivatives and polyacrylates containing amine side groups.

Exemplary non-ionic associative polymers include celluloses modified with groups comprising at least one fatty chain, for instance hydroxyethyl celluloses modified with groups comprising at least one fatty chain, such as alkyl groups, e.g. $C_8-C_{22}$ alkyl groups, arylalkyl and alkylaryl groups, such as cetyl hydroxyethyl cellulose, also known as Natrosol® Plus (sold by the company Ashland); Bermocoll EHM 100 (sold by the company Berol Nobel), Amercell Polymer HM-1500® sold by Amerchol (hydroxyethylcellulose modified with a polyethylene glycol (15) nonylphenyl ether group, sold by the company Amerchol), celluloses modified with polyalkylene glycol alkylphenyl ether groups, guars such as hydroxypropyl guar, optionally modified with groups comprising at least one fatty chain such as an alkyl chain, for example JAGUAR® XC-95/3 (C14 alkyl chain, sold by the company Rhodia Chimie); Esaflor HM 22 (C22 alkyl chain, sold by the company Lamberti); RE210-18 (C14 alkyl chain) and RE205-1 (C20 alkyl chain, sold by the company Rhodia Chimie), copolymers of vinylpyrrolidone and of fatty-chain hydrophobic monomers, for instance Antaron® or Ganex® V216 (vinylpyrrolidone/hexadecene copolymers); Antaron® or Ganex® V220 (vinylpyrrolidone/ eicosene copolymers), sold by the company I.S.P., copolymers of $C_1-C_6$ alkyl methacrylates or acrylates and of amphiphilic monomers comprising at least one fatty chain, and copolymers of hydrophilic methacrylates or acrylates and of hydrophobic monomers comprising at least one fatty chain, for instance the polyethylene glycol methacrylate/ lauryl methacrylate copolymer; polymers with an aminoplast ether skeleton containing at least one fatty chain, such as the Pure Thix® nonionic associative water phase thickeners sold by the company Southern Clay Products, Inc.

Associative polyurethanes may also be chosen in various exemplary and non-limiting embodiments. These are non-ionic block copolymers comprising in the chain both hydrophilic blocks usually of polyoxyethylene nature, and hydrophobic blocks that may be aliphatic sequences alone and/or cycloaliphatic and/or aromatic sequences. Associative polyurethanes comprise at least two hydrocarbon-based lipophilic chains containing from $C_6$ to $C_{30}$ carbon atoms, separated by a hydrophilic block, the hydrocarbon-based chains optionally being pendent chains or chains at the end of a hydrophilic block. For example, it is possible for one or more pendent chains to be provided. In addition, the polymer may comprise a hydrocarbon-based chain at one or both ends of a hydrophilic block. The associative polyurethanes may be arranged in triblock or multiblock form. The hydrophobic blocks may thus be at the each end of the chain (for example, triblock copolymer with a hydrophilic central block) or distributed both at the ends and within the chain (for example, multiblock copolymer). These polymers may also be graft polymers or starburst polymers. For example, the associative polyurethanes may be triblock copolymers in which the hydrophilic block is a polyoxyethylene chain containing from 50 to 1000 oxyethylene groups.

By way of non-limiting example, associative polymers of the polyurethane polyether type that may be used include the polymer $C_{16}—OE_{120}-C_{16}$ from Servo Delden (under the name SER AD FX1100), which is a molecule containing a urethane function and having a weight-average molecular weight of 1300), OE being an oxyethylene unit, Nuvis® FX 1100 (European and US INCI name "Steareth-100/PEG-136/HMDI Copolymer" sold by the company Elementis Specialties), and also Acrysol RM 184® (sold by the company Rohm and Haas); Elfacos® T210® (C12-C14 alkyl chain) and Elfacos® T212® (C18 alkyl chain) sold by the company Akzo. Further exemplary associative polymers that may be chosen include RHEOLATE® 205 containing a urea function, sold by Rheox, or RHEOLATE® 208 or 204, or RHEOLATE® FX1100 from Elementis. The product DW 1206B from Rohm & Haas containing a $C_{20}$ alkyl chain with a urethane bond, sold at a solids content of 20% in water, may also be used.

In yet further exemplary embodiments, solutions or dispersions of these polymers, especially in water or in aqueous-alcoholic medium, may be chosen. Examples of such polymers include SER AD FX1010, SER AD FX1035 and SER AD 1070 from Servo Delden, and RHEOLATE® 255, RHEOLATE® 278 and RHEOLATE® 244 sold by Rheox. Further examples include the products ACULYN™ 46, DW 1206F and DW 1206J, and also ACRYSOL RM 184 or ACRYSOL 44 from Rohm & Haas, and BORCHIGEL LW 44 from Borchers.

In yet further embodiments, the second thickener is chosen from polymers of natural origin such as, for example, thickening polymers comprising at least one sugar unit, for instance nonionic guar gums, optionally modified with C1-C6 hydroxyalkyl groups; biopolysaccharide gums of microbial origin, such as scleroglucan gum (also known as sclerotium gum) or xanthan gum; gums derived from plant exudates, such as gum arabic, ghatti gum, karaya gum, gum tragacanth, carrageenan gum, agar gum and carob gum, ceratonia siliqua gum and cyamopsis tetragonoloba (guar) gum; pectins; alginates; starches; hydroxy(C1-C6)alkylcelluloses and carboxy(C1-C6)alkylcelluloses.

Non-limiting examples of nonionic, unmodified guar gums that may be used in various embodiments include Guargel D/15 (Noveon); Vidogum GH 175 (Unipectine), Meypro-Guar 50 and JAGUAR® C (Meyhall/Rhodia Chimie). Non-limiting examples of nonionic modified guar gums include Jaguar® HP8, HP60, HP120, DC 293 and HP 105 (Meyhall/Rhodia Chimie); and Galactasol 4H4FD2 (Ashland).

Further examples of useful thickening agents include scleroglucans, for example, Actigum™ CS from Sanofi Bio Industries; Amigel from Alban Muller International, and also the glyoxal-treated scleroglucans described in FR2633940); xanthan gums, for instance Keltrol®, Keltrol® T, Keltrol® Tf, Keltrol® Bt, Keltrol® Rd, Keltrol® Cg (Nutrasweet Kelco), Rhodicare® S and Rhodicare® H (Rhodia Chimie); starch derivatives, for instance Primogel® (Avebe); hydroxyethylcelluloses such as Cellosize® QP3L, QP4400H, QP30000H, HEC30000A and Polymer PCG10 (Amerchol), Natrosol™ 250HHR®, 250MR, 250M, 250HHXR, 250HHX, 250HR, HX (Hercules) and Tylose® H1000 (Hoechst); hydroxypropylcelluloses, for instance Klucel® EF, H, LHF, MF and G (Ashland); carboxymethylcelluloses, for instance Blanose® 7M8/SF, refined 7M, 7LF, 7MF, 9M31F, 12M31XP, 12M31P, 9M31XF, 7H, 7M31, 7H3SXF (Ashland), Aquasorb® A500 (Hercules), Ambergum® 1221 (Hercules), Cellogen® HP810A, HP6HS9 (Montello) and Primellose® (Avebe).

Exemplary modified nonionic guar gums may, for example, be modified with C1-C6 hydroxyalkyl groups. Exemplary hydroxyalkyl groups may include hydroxymethyl, hydroxyethyl, hydroxypropyl and hydroxybutyl groups.

Guar gums are well known in the state of the art and may, for example, be prepared by reacting the corresponding alkene oxides, such as for example propylene oxides, with guar gum so as to obtain a guar gum modified with hydroxypropyl groups. The hydroxyalkylation ratio, which corresponds to the number of alkylene oxide molecules consumed to the number of free hydroxyl functional groups present on the guar gum, may in at least certain exemplary embodiments vary from about 0.4 to about 1.2.

Exemplary and non-limiting nonionic guar gums, optionally modified with hydroxyalkyl groups, include those sold under the trade names JAGUAR® HP8, JAGUAR® HP60 and JAGUAR® HP120, JAGUAR® DC 293 and JAGUAR® HP 105 by the company RHODIA CHIMIE (RHODIA CHIMIE), and under the name GALACTASOL™ 4H4FD2 by the company ASHLAND.

Guar gums may also be modified with a quaternary ammonium group. Guar gums modified as such include Guar Hydroxypropyltrimonium Chloride, also known under the tradename JAGUAR® C-13S (RHODIA CHIMIE).

Exemplary and non-limiting celluloses include hydroxyethylcelluloses and hydroxypropylcelluloses. The products sold under the names KLUCEL EF, KLUCEL H, KLUCEL LHF, KLUCEL MF, KLUCEL G, by the company ASHLAND, CELLOSIZE POLYMER PCG-10 by the company AMERCHOL, may be chosen in various embodiments.

Exemplary, non-limiting thickening polysaccharides may be chosen from glucans, modified or unmodified starches (such as those derived, for example, from cereals such as wheat, corn or rice, vegetables such as golden pea, tubers such as potato or cassava), amylose, amylopectin, glycogen, dextrans, celluloses and derivatives thereof (methylcelluloses, hydroxyalkylcelluloses, ethylhydroxyethylcelluloses), mannans, xylans, lignins, arabans, galactans, galacturonans, chitin, chitosans, glucoronoxylans, arabinoxylans, xyloglucans, glucomannans, pectic acids and pectins, arabinogalactans, carrageenans, agars, gums arabic, gums tragacanth, Ghatti gums, Karaya gums, carob gums, galactomannans such as guar gums and their nonionic derivatives (hydroxypropylguar), and mixtures thereof.

Further, exemplary thickening agents include silicas, optionally hydrophobic, such as those described in EP-A-898960, and for example marketed as AEROSIL® R812 by the company Degussa, CAB-O-SIL TS-530, CAB-O-SIL TS-610, CAB-O-SIL TS-720 by the company Cabot, AEROSIL® R972, AEROSIL® R974 by the company Degussa; clays, such as montmorillonite, modified clays such as the bentones for example, stearalkonium hectorite, stearalkonium bentonite; polysaccharide alkyl ethers (optionally with the alkyl group having from 1 to 24 carbon atoms, for example from 1 to 10 carbon atoms, as a further example from 1 to 6 carbon atoms, and as yet a further example from 1 to 3 carbon atoms) such as those described in document EP-A-898958.

The second thickener may also include rheology modifiers. In accordance with the disclosure, rheology modifiers may, in various exemplary embodiments, be chosen from Polyacrylamide(and)C13-14 Isoparaffin(and)Laureth-7 (Sepigel™ 305 from Seppic), Hydroxypropyl Guar (JAGUAR® HP105 from Rhodia), Cyamopsis Tetragonoloba (Guar) Gum (Supercol U Guar Gum from Ashland), Acrylates/C10-30 Alkyl Acrylate Crosspolymer (Carbopol® Ultrez 20 Polymer from Lubrizol), Acrylates/C10-30 Alkyl Acrylate Crosspolymer (Permulen™ TR-1 from Lubrizol), Polyacrylate Crosspolymer-6 (Sepimax Zen from Seppic), Sclerotium Gum (Amigum from Alban Muller), Xanthan Gum(and)Ceratonia Siliqua Gum (Nomcort CG from Nisshin Oil Lio), Hydroxypropyl Guar (Jaguar® HP8 from Rhodia), Guar Hydroxypropyl Trimonium Chloride (Jaguar® C-13-S from Rhodia), Hydroxyethyl Cellulose (Natrosol® 250 MR from Ashland).

When anionic thickening agents are used, they are generally neutralized before being included in or as they are added to the compositions of the disclosure. Such anionic thickening agents may be neutralized by employing traditional neutralizing agents such as alkanolamines, for example, monoethanolamine and diethanolamine; aminomethyl propanol; basic amino acids, for example arginine and lysine; and ammonium compounds and their salts.

Cationic thickening agents of the disclosure may also be chosen from non-associative cationic polymers such as dimethylaminoethyl methacrylate homopolymers quaternized with methyl chloride or dimethylaminoethyl methacrylate copolymers quaternized with methyl chloride and acrylamide. Among the homopolymers of this type, mention may be made of the products sold under the names Salcare SC95 and Salcare SC96 by the company Ciba and SYNTHALEN® CR by the company 3V Sigma (chemical name: methacryloylethyl trimethyl ammonium chloride homopolymer, INCI name: polyquaternium-37). Among the copolymers of this family, mention may be made of the product Salcare S C92 sold by Ciba or the product PAS 5 194 sold by Hoechst.

Another suitable example of a cationic thickening agent is a product known by the INCI name of polyacrylate-1 crosspolymer (Carbopol® Aqua CC, from the company, Lubrizol).

In a particular embodiment, the composition of the invention includes a second thickener, preferably selected from modified or unmodified carboxyvinyl polymers, such as the products sold by Goodrich under the name CARBOPOL® (CTFA name: carbomer).

When present in the instant compositions, the additional thickener is present in an amount of from about 0.01% to about 2% by weight, or such as from about 0.05% to about 1.5% by weight, typically about 0.1% to about 1% by weight, relative to the total weight of the composition.

Cationic Conditioning Agent (d)

The compositions of the invention also include at least one cationic conditioning agent. The at least one cationic conditioning agent may be chosen, for example, from a polymer, including for example homopolymers and copolymers, as well as from cationic surfactants, cationic amines and cationic silicones.

Non-limiting examples of polymers that can be used in the current compositions include: cationic cellulose derivatives, such as for example polyquaternium-10 ("PQ-10"); cationic gum derivatives such as for example gum derivatives, including particularly guar hydroxypropyltrimonium chloride; polymer derivatives of diallyldimethyl ammonium chloride ("poly-DADMAs") and of methacrylamidopropyltrimethylammonium chloride ("poly-MAPTACs"), and having the following formulas:

MAPTAC:

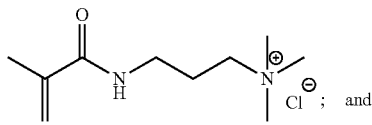

and

DADMAC:

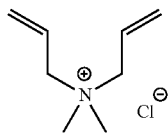

Non-limiting examples of poly-DADMAs and poly-poly-MAPTACs include, polyquaternium-4 (PQ-4), polyquaternium-5 (PQ-5), polyquaternium-6 (PQ-6), polyquaternium-7 (PQ-7), polyquaternium-22 (PQ-22), polyquaternium-37 (PQ-37), polyquaternium-39 (PQ-39), polyquaternium47 (PQ-47) and polyquaternium-53 (PQ-53), and mixtures thereof. PQ-10 and PQ-7 are particularly useful in the instant compositions.

Cationic proteins, such as, for example, hydroxypropyltrimonium hydrolyzed wheat protein are also useful as cationic conditioning agents.

Amine-functionalized silicones may also be used as cationic conditioning agents in the instant compositions. Non-liming examples of amine-functionalized silicones include amodimethicone, bis-aminopropyl dimethicone, trimethyl silylamodimethicone, and mixtures thereof, more particularly amodimethicone.

Amino Silicones

The term "amino silicone" means any polyaminosiloxane, i.e. any polysiloxane comprising at least one primary, secondary or tertiary amine function or a quaternary ammonium group. Preferably, the amino silicone(s) used in the cosmetic composition according to the present invention are selected from (A)-(D) as described below.

Amino silicones are described, for example, in US2011/0155163 and US2011/155164, both of which are herein incorporated by reference.

(A) Compounds Corresponding to Formula

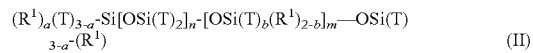

(II)

in which:
T is a hydrogen atom or a phenyl, hydroxyl (—OH) or $C_1$-$C_8$ alkyl radical, and preferably methyl, or a $C_1$-$C_8$ alkoxy, preferably methoxy;
a is the number 0 or an integer from 1 to 3, and preferably 0;
b is 0 or 1, and in particular 1;
m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;
$R^1$ is a monovalent radical of formula —$C_qH_{2q}$L in which q is a number from 2 to 8; and L is an optionally quaternized amino group selected from the following groups:
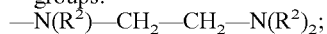
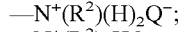
in which $R^2$ denotes a hydrogen atom, a phenyl, a benzyl or a saturated monovalent hydrocarbon-based radical, for example a $C_1$-$C_{20}$ alkyl radical, and $Q^-$ represents a halide ion, for instance fluoride, chloride, bromide or iodide.

In a particular embodiment, the amino silicones corresponding to the definition of formula (II) are selected from the compounds corresponding to formula (III) below:

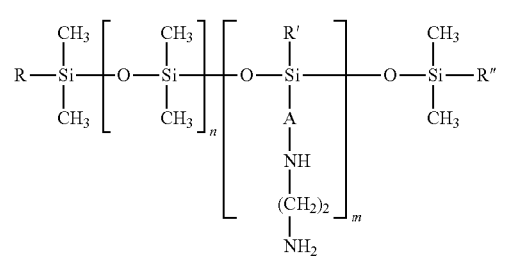

(III)

in which
R, R' and R", which may be identical or different, denote a $C_1$-$C_4$ alkyl radical, preferably $CH_3$; a $C_1$-$C_4$ alkoxy radical, preferably methoxy; or OH;
A represents a linear or branched, $C_3$-$C_8$ and preferably $C_3$-$C_6$ alkylene radical;
m and n are integers dependent on the molecular weight and whose sum is between 1 and 2000.

According to a first possibility, R, R', R", which may be identical or different, represent a $C_1$-$C_4$ alkyl or hydroxyl radical, A represents a $C_3$ alkylene radical and m and n are such that the weight-average molecular weight of the compound is between 5000 and 500000 approximately. Compounds of this type are referred to in the CTFA dictionary as "aminodimethicones".

According to a second possibility, R, R' and R", which may be identical or different, represent a $C_1$-$C_4$ alkoxy or hydroxyl radical, at least one of the radicals R or R" is an alkoxy radical and A represents a $C_3$ alkylene radical. The hydroxy/alkoxy molar ratio is preferably between 0.2/1 and 0.4/1 and advantageously equal to 0.3/1. Moreover, m and n are such that the weight-average molecular weight of the compound is between 2000 and $10^6$. More particularly, n is between 0 and 999 and m is between 1 and 1000, the sum of n and m being between 1 and 1000. An example of this category of compounds is the product BELSIL® ADM 652 sold by Wacker.

According to a third possibility, R and R", which are different, represent a $C_1$-$C_4$ alkoxy or hydroxyl radical, at least one of the radicals R or R" is an alkoxy radical, R' represents a methyl radical and A represents a $C_3$ alkylene radical. The hydroxy/alkoxy molar ratio is preferably between 1/0.8 and 1/1.1 and advantageously equal to 1/0.95. Moreover, m and n are such that the weight-average molecular weight of the compound is between 2000 and 200000. More particularly, n is between 0 and 999 and m is between 1 and 1000, the sum of n and m being between 1 and 1000. An example of this category of compounds is product FLUID WR® 1300 sold by Wacker.

According to a fourth possibility, R and R" represent a hydroxyl radical, R' represents a methyl radical and A is a $C_4$-$C_8$ and preferably $C_4$ alkylene radical. Moreover, m and n are such that the weight-average molecular weight of the compound is between 2000 and $10^6$. More particularly, n is between 0 and 1999 and m is between 1 and 2000, the sum of n and m being between 1 and 2000. As example of a product of this type is DC 28299 sold by Dow Corning.

The molecular weight of these silicones is determined by gel permeation chromatography (ambient temperature, polystyrene standard; μ styragem columns; eluent THF; flow rate 1 mm/m; 200 μl of a solution containing 0.5% by weight of silicone in THF are injected, and detection is performed using a refractometer and a UV meter).

A particular product of formula (II) is the polymer known in the CTFA dictionary (7th edition, 1997) as "trimethylsilylamodimethicone", corresponding to formula (IV)

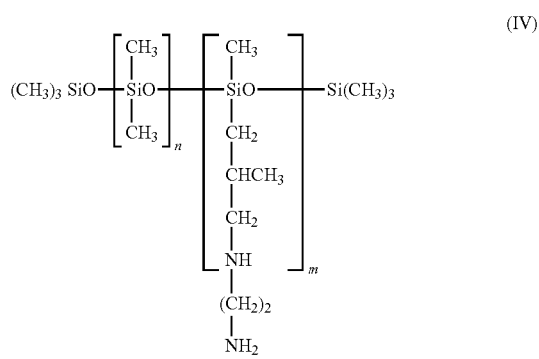

in which n and m have the meanings given above in accordance with formula (II) or (III) above.

Such compounds are described, for example, in EP 0 095 238, which is herein incorporated by reference. A compound of formula (IV) is sold, for example, under the name Q2-8220 by the company OSI.

(B) the Second Type of Amino Silicone Compounds Correspond to Formula (V)

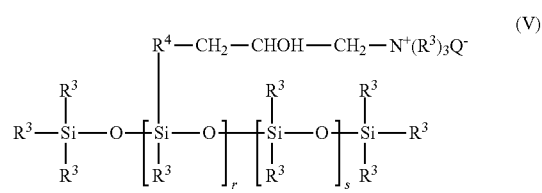

in which:

$R^3$ represents a $C_1$-$C_{18}$ monovalent hydrocarbon-based radical, and in particular a $C_1$-$C_{18}$ alkyl or $C_2$-$C_{18}$ alkenyl radical, for example methyl;

$R^4$ represents a divalent hydrocarbon-based radical, especially a $C_1$-$C_{18}$ alkylene radical or a divalent $C_1$-$C_{18}$, and for example $C_1$-$C_8$, alkylenoxy radical;

$Q^-$ is a halide ion, in particular chloride;

r represents a mean statistical value from 2 to 20 and in particular from 2 to 8; and s represents a mean statistical value from 20 to 200 and in particular from 20 to 50.

Such compounds are described more particularly in U.S. Pat. No. 4,185,087, which is herein incorporated by reference. A compound falling within this class is the product sold by the company Union Carbide under the name Ucar Silicone ALE 56.

(C) Quaternary Ammonium Silicones of Formula (VI) are Another Type of Silicone Useful in the Invention:

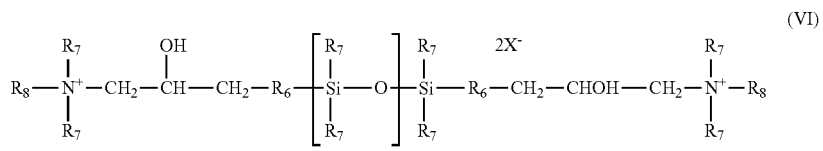

in which:

R$_7$, which may be identical or different, represent a monovalent hydrocarbon-based radical containing from 1 to 18 carbon atoms, and in particular a C$_1$-C$_{18}$ alkyl radical, a C$_2$-C$_{18}$ alkenyl radical or a ring comprising 5 or 6 carbon atoms, for example methyl;

R$_6$ represents a divalent hydrocarbon-based radical, especially a C$_1$-C$_{18}$ alkylene radical or a divalent C$_1$-C$_{18}$, and for example C$_1$-C$_8$, alkylenoxy radical linked to the Si via an SiC bond;

R$_8$, which may be identical or different, represent a hydrogen atom, a monovalent hydrocarbon-based radical containing from 1 to 18 carbon atoms, and in particular a C$_1$-C$_{18}$ alkyl radical, a C$_2$-C$_{18}$ alkenyl radical or a radical —R$_6$—NHCOR$_7$;

X$^-$ is an anion such as a halide ion, especially chloride, or an organic acid salt (acetate, etc.); and r represents a mean statistical value from 2 to 200 and in particular from 5 to 100.

These silicones are described, for example, in patent application EP-A 0 530 974, which is herein incorporated by reference. An example of the compound of formula (VI) is the product referenced in the CTFA dictionary (1997 edition) as Quaternium 80. Such a product is marketed by the company Evonik Goldschmidt under the names ABIL QUAT 3272 or 3474.

(D) Formula (VII) Below Provides Another Example of Amino Silicones Useful in the Invention:

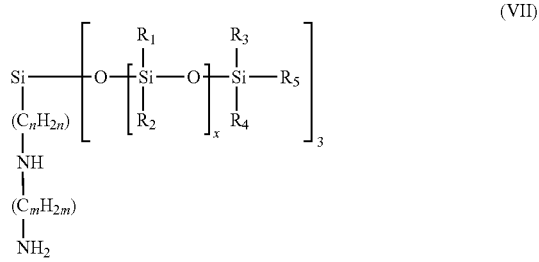

(VII)

in which:

R$_1$, R$_2$, R$_3$ and R$_4$, which may be identical or different, denote a C$_1$-C$_4$ alkyl radical or a phenyl group, R$_5$ denotes a C$_1$-C$_4$ alkyl radical or a hydroxyl group, n is an integer ranging from 1 to 5, m is an integer ranging from 1 to 5, and in which x is selected such that the amine number is between 0.01 and 1 meq/g.

Amino silicone(s) that are particularly useful in the invention include polysiloxanes containing amine groups, such as the compounds of formula (III) or of formula (IV), and even more particularly the silicones containing quaternary ammonium groups of formula (VI).

Non-limiting examples of particularly useful silicones include aminodimethicones, such as the products available from the company Wacker under the name FLUID® (for example FLUID® WR 1300) and BELSIL® (for example BELSIL® ADM LOG1) and a product available from Momentive Performance Material under the name SIL-SOFT®. Also useful is trimethylsilylamodimethicone (such as Q@-8220 available from OSI).

In an embodiment, the cationic conditioning agent is selected from at least one polymer.

In a particular embodiment, the cationic conditioning agent is selected from PQ-7, PQ-10, amodimethicone and mixtures thereof.

The at least one cationic conditioning agent is present in the compositions of the invention in an amount of from about 0.01% to about 2% by weight, such as from about 0.05% to about 1.75% by weight, typically from about 0.1% to about 1.5%, by weight, more typically from about 1% to about 1.3%, by weight, based on the total weight of the composition as a whole.

Nonionic Surfactant (e) (Optional)

The compositions of the invention optionally may include at least one non-ionic surfactant. These surfactants are known for providing good cleaning properties. The at least one nonionic surfactant useful in the cleansing compositions disclosed herein is selected from: alkyl polyglucosides; ethylene glycol, propylene glycol, glycerol, polyglyceryl esters and their ethoxylated derivatives (herein jointly referred to as "glycol esters"); amine oxides; and mixtures of the foregoing.

Alkyl polyglucosides useful in the compositions of the invention include those having the following formula:

$$R^1\text{—O—}(R^2O)n\text{-}Z(x) \qquad (XXX)$$

wherein

R$^1$ is an alkyl group having 8-18 carbon atoms;

R$^2$ is an ethylene or propylene group;

Z is a saccharide group with 5 to 6 carbon atoms;

n is an integer from 0 to 10; and x is an integer from 1 to 5.

Non-limiting examples of alkyl poly glucosides useful in the compositions of the invention include lauryl glucoside, octyl glucoside, decyl glucoside, coco glucoside, sucrose laurate, caprylyl/capryl glucoside, sodium lauryl glucose carboxylate, and mixtures thereof. Typically, the at least one alkyl polyglucoside compound is selected from the group consisting of lauryl glucoside, decyl glucoside, coco glucoside, and mixtures thereof.

In a particular embodiment the nonionic surfactant is an alkyl poly glucoside selected from decyl glucoside and coco glucoside, and mixtures thereof.

Non-limiting examples of glycol esters useful in the compositions of the invention include those described in M. R. Porter et al., Handbook of Surfactants, Ch. 7, § 7.12, pp. 231-235 ($2^{nd}$ Ed. 1994), which is herein incorporated by reference. Preferred glycol esters have HLB values between about 9 and about 18. Particular glycol esters useful in the compositions of the invention include PEG-8 glyceryl laurate, polysorbate-40, polyglyceryl-5 laurate, and mixtures thereof.

Amine oxides useful in the compositions of the invention include those having the formulas (XXXIA) and (XXXIB)

$$R\text{—N(CH3)}_2\text{-O} \qquad (XXXIA), \text{ and}$$

$$R\text{—CO—NH(CH}_2)_n\text{—N(CH3)}_2\text{-O} \qquad (XXXIB)$$

wherein

R is an alkyl group having 8-18 carbon atoms; and n is an integer from 1 to 3.

A non-limiting example of a particular amine oxide is lauramine oxide.

In a particular embodiment, a nonionic surfactant is present in the composition and is selected from alkyl polyglucosides such as, for example, decyl glucoside, coco glucoside and mixtures thereof.

The at least one nonionic surfactant may be used in an amount of from about 0% to about 2%. In an embodiment the at least one nonionic surfactant is present at 0%. In another embodiment the at least one nonionic surfactant is present in an amount from about 0.5% to about 1.5%, and more typically about 1%, including all ranges and sub ranges therebetween, by weight, relative to the weight of the final composition.

Additives/Further Optional Additional Components

The composition of the present disclosure may additionally include any other adjuvant or additive that is usually used in the field of self-cleaning products, in particular shampoos. A person skilled in the art would know which adjuvants and/or additives to select to achieve the desired results (e.g. preservatives) without adversely affecting the properties of claimed emulsions. For example, such additives include pH adjusting agents, preserving agents, sequestrants and chelators, consistency regulators (e.g. isopropyl alcohol), thickeners, pH-regulators, antioxidants, fragrances, dyestuffs such as soluble dyes and pigments, optical brighteners, electrolytes and stabilizers (e.g. sodium chloride, glycerin), plant extracts, proteins, amino acids, vitamins, glycols, emollients, derivatives of the foregoing, and mixtures thereof. A non-exhaustive list of such additives is provided, for example in US2012/0308492 at [0079]-[0080] and US2006/0217283 at [0084]-[0087], herein incorporated by reference. Additional examples of additives may be found in the International Cosmetic Ingredient Dictionary and Handbook (9$^{th}$ ed. 2002, as subsequent editions).

Non-limiting examples of pH adjusting agents includes potassium acetate, potassium hydroxide, sodium carbonate, sodium hydroxide, phosphoric acid, succinic acid, sodium citrate, citric acid, boric acid, lactic acid, sodium hydrogen carbonate, ethanol amines, and mixtures thereof. In a particular embodiment, the pH adjusting agent is selected from potassium hydroxide, sodium hydroxide, ethanol amines, and mixtures thereof. In a particular embodiment, the pH adjusting agent is selected from sodium hydroxide, potassium hydroxide and ethanol amines, and mixtures thereof.

on-limiting examples of useful preservatives include ethanol, polyvinyl alcohol, phenoxyethanol, benzyl alcohol, salicylic acid, sodium benzoate, benzoic acid, caprylyl glycol, methyl paraben, propyl paraben, ethylhexylglycerin, 1,3-propanediol, cholorphensin, methylchloroisothiazolinone, methylisothiazolinone, benzalkonium chloride, polyaminopropyl biguanide, and mixtures thereof. In a particular embodiment, the pH adjusting agent is selected from cholorphensin, methylchloroisothiazolinone, methylisothiazolinone, benzalkonium chloride, polyaminopropyl biguanide, and mixtures thereof.

Chelating agents and antioxidants are ingredients which assist in preventing or retarding spoilage. Examples of antioxidants suitable for use in the present composition are potassium sulfite, sodium bisulfite, sodium erythrobate, sodium metabisulfite, sodium sulfite, propyl gallate, cysteine hydrochloride, butylated hydroxytoluene, butylated hydroxyanisole, and mixtures thereof. Suitable chelators include salts of ethylenediaminetetraacetic acid ("EDTA"), tetrasodium EDTA, butylated hydroxytoluene ("BHT"), and mixtures thereof.

Notwithstanding that the numerical ranges and parameters setting forth the broad scope of the invention are approximations, the numerical values set forth in the specific examples are reported as precisely as possible. The following examples are intended to illustrate the invention without limiting the scope as a result. The percentages are given on a weight basis unless otherwise specified.

Examples

Preparation:
1. Water and optional thickening agent were combined and mixed well.
2. Anionic surfactants were added to 1 and mixed until uniform.
3. Cationic polymers were added and mixed well until fully dispersed.
4. The resulting composition of 3 was heated to 75-80° C.
5. Any remaining surfactants and pearlizing agents were added and the composition was mix well until all components were fully melted.
6. The composition was then cooled to room temperature.
7. Fragrance and silicone were added and mixed well.
8. Betaine and preservative were added and mixed well until uniform.
9. Hydrophobically-modified acrylic acid based copolymer was added and mixed well until uniform.
10. pH and viscosity were adjusted as needed.

The resulting compositions were either clear or adjusted to be pearlescent/opaque as desired. The compositions were viscous with a honey-like flow.

TABLE 1

Examples 1-5: Inventive Compositions Having Various Surfactant Amounts/Ratios

| INCI Name | Example 1 | Example 2 | Example 3 | Example 4 | Example 5 |
|---|---|---|---|---|---|
| sodium lauroyl methyl isethionate (a) | | 2.68 | 3.50 | 3.50 | 2.82 |
| sodium lauroyl sarcosinate (a) | 1.50 | 1.50 | | | |
| sodium lauryl sulfoacetate (a) | 1.75 | 1.75 | 0.70 | 0.34 | 0.27 |
| disodium laureth sulfosuccinate (a) | 4.50 | 4.50 | 1.80 | 0.86 | 0.70 |
| sodium cocoyl isethionate (a) | 2.64 | | | | |
| sodium cocoyl glycinate (a) | | | | 1.00 | 0.81 |
| decyl glucoside (e) | 0.93 | | 1.00 | 1.00 | 1.00 |
| cocamidopropyl betaine (b) | | | 3.50 | 3.50 | 4.60 |
| coco-betaine (b) | 4.55 | 4.65 | | | |
| acrylates/beheneth-25 methacrylate copolymer (c) NOVETHIX ™ L-10 POLYMER (Lubrizol) | 0.11 | 0.30 | 0.50 | 1.00 | 1.00 |
| carbomer | 0.20 | 0.20 | 0.20 | 0.20 | 0.20 |
| polyquaternium-10 (d) | 0.64 | 0.64 | 0.18 | 0.18 | 0.18 |
| polyquaternium-7 (d) | | | 0.45 | 0.45 | 0.45 |
| amodimethicone (d) | 0.58 | 0.58 | 0.58 | 0.58 | 0.58 |

TABLE 1-continued

Examples 1-5: Inventive Compositions Having Various Surfactant Amounts/Ratios

| INCI Name | Example 1 | Example 2 | Example 3 | Example 4 | Example 5 |
|---|---|---|---|---|---|
| Additives | as needed | as needed | as needed | as needed | as needed |
| water | q.s. | q.s. | q.s. | q.s. | q.s. |
| Total anionic surfactants (a) | 10.39 | 10.43 | 6 | 5.7 | 4.6 |
| Total amphoteric surfactants (b) | 4.55 | 4.65 | 3.5 | 3.5 | 4.60 |
| Anionic (a)/amphoteric (b) | 2.28 | 2.24 | 1.71 | 1.63 | 1:1 |
| Anioic (a) + amphoteric (b) + nonionic (e) surfactants | 15.86 | 15.08 | 10.50 | 10.20 | 10.20 |
| [Anioic (a) + amphoteric (b) + nonionic (e) surfactants]/ thickener (c) | 144.18 | 50.27 | 20.96 | 10.21 | 10.20 |

TABLE 2

Comparative Example

| INCI Name | Comparative 1 |
|---|---|
| sodium lauroyl methyl isethionate (a) | 5.14 |
| sodium lauryl sulfoacetate (a) | 0.49 |
| disodium laureth sulfosuccinate (a) | 1.27 |
| sodium cocoyl glycinate (a) | 1.47 |
| decyl glucoside (e) | 1.00 |
| cocamidopropyl betaine (b) | 0.86 |
| acrylates/beheneth-25 methacrylate copolymer (c) | 1.00 |
| carbomer | 0.20 |
| polyquaternium-10 (d) | 0.18 |
| polyquaternium-7 (d) | 0.45 |
| amodimethicone (d) | 0.58 |
| additives | as needed |
| water | q.s. |
| Total anionic surfactants (a) | 8.37 |
| Total amphoteric surfactants (b) | 0.86 |
| Anionic (a)/amphoteric (b) | 9.7 |
| Anionic (a) + amphoteric (b) + nonionic (e) surfactants | 10.20 |
| [Anionic (a) + amphoteric (b) + nonionic (e) surfactants]/ thickener (c) | 10.20 |

Evaluation and Protocols

I. Cationic Deposition Study:

Protocol

Deposition of cationic conditioning agents was assessed using an established method in the art referred to as the Rubine Dye Test. The test uses an anionic red dye (red 80) which associates with cationic materials deposited on the hair by the test product. To easily observe the dye uptake, piedmont white hairs supplied by International Hair Importers is use in this test. Deposition of cationic agents is then determined by the amount of red dye remaining on the hair fibers after rinsing. The darker the pink or red color transferred onto the hair the higher the amount of cationic surfactant deposition. See, e.g., U.S. Pat. No. 7,048,770, which also describes such test.

Concentrated Red 80 Solution:

4.67 g of Direct Red 80+1.25 g of acetic acid+1 kg of water

Diluted Red 80 Solution (20% solution):

200 g of concentrated solution+800 g of DI water

Protocol for treating and staining the swatches used in the experiments:

1. Hair (swatch) was rinsed under water for 30 seconds.
2. Hair swatches were then lathered for 30 seconds using 1:1 product/swatch ratio by weight.
3. Swatches were rinsed for 30 seconds under running room temperature (RT) water while using fingers to remove excess product or foam.
4. Swatches were then place on a towel to remove access water.
5. Hair swatches were submerged in the red 80 dye solution (20× the weight of the swatch) for 1 minute.
6. Swatches were rinsed for 20 seconds under running RT water.
7. The intensity of the color of the hair swatch was measured using a Konica Minolta Spectrophotometer (Model CM-2600d).

Color Scales:

The color scales used for this test were the Hunter L,a,b scales. These are 3-dimensional scales. These scales are based on the opponent-colors theory that states that the red, green and blue human eye cone responses are re-mixed into black-white, red-green, and yellow-blue, opponent coders as they move up the optic nerve to the brain.

The L,a,b type of scales simulate this as:

L (lightness) axis—0 is black, 100 is white a (red-green) axis—positive values are red; negative values are green and 0 is neutral b (yellow-blue) axis—positive values are yellow; negative values are blue and 0 is neutral C (chroma saturation)—0 is no color value. Numbers can only be positive numbers and indicate greater and greater amounts of color.

h (hue) axis—0° is red, 90° is yellow, 180° is green and 270° is blue.

All colors that can visually be perceived can be measured in L,a,b. This test specifically refers to the L values as it is the measure of black versus white. As 0 is black, the lower the L value, the darker the color. Hue is measured as h* which is a measure of the degree of the angle from red.

For this experiment, only the "a" (red-green) value was analyzed to assess the change in the redness of the hair swatches. An increase in the value of "a" (that is a higher Δa in the table below) indicates more redness demonstrating increased deposition and retention of cationic agent onto the hair swatch. The results of this test are summarized in Table 3 below.

TABLE 3

Cationic Deposition Comparison

| Sample | Δa (one wash) | Δa (2 washes) |
|---|---|---|
| Comparative 1 | 9.95 | 11.18 |
| Example 4 | 8.17 | 10.37 |

Results:

As is shown in Tables 1 and 2, the inventive composition of Example 4//and Comparative 1 both contain the same ingredients, same level of total surfactants (anionic (a)+ amphoteric (b)+nonionic (c)) and same level of polymers (thickeners and cationic agents). However, in contrast to Comparative Composition 1, in the inventive composition of Ex. 4, the ratio of anionic surfactants (a) to amphoteric surfactants (b) is less than 9.5. This ratio leads to an optimized detergency and conditioning balance as is shown by the composition of Ex 4 as is further discussed below.

When the ratio of anionic surfactants (a) to amphoteric surfactant (b) is equal to or greater than 9.5 (Comparative 1), the deposition of conditioning agents is increased but the detergency is decreased. This is shown in Table 3 by the fact that upon rewashing with Comparative 1 (2 washes), the deposition of cationic agents (measured by $\Delta a$) is very high. This shows that the shampoo of Comparative 1 is not washing out enough of the deposits (less detergency) and is continuing build up cationic deposition. This is undesirable as the hair becomes too greasy and weighted down. This result is also unexpected as anionic surfactants are known for high detergency and low deposition of conditioning agents. See, Liquid Detergents (Surfactant Science) (2005, Kuo-Yann Lai, Ed.) at p. 10. Without being bound by theory, it is postulated that this behavior is a result of how the anionic surfactants interact with the at least one thickener selected from hydrophobically-modified acrylic acid based copolymer (c).

In contrast to conventional expectations, the compositions of the invention having a higher ratio of anionic to amphoteric surfactants, but less than a ratio of 9.5:1, actually yield increased deposition of the cationic conditioning polymers thereby yielding enhanced and balanced conditioning effects.

II. Panel/Sensory Testing

Protocol

Panel testing was conducted on 12 people and test products were evaluated by expert hair stylists. Test products were blinded so the stylists did not know the name or nature of each product. Test shampoo was randomly applied side by side to one half of the head and compared to the standard on the remaining half. This test protocol was used to evaluate foam, detergency, conditioning and appearance of test subjects' hair. The scales for measuring these parameters were as follows:

Flash Foam—rate of foam generation when test shampoo is first applied to hair. The scale is from 0-5, 0 being the slowest and 5 being the fastest.
Distribution Ease—the difficulty of spreading and distributing of the test product over the entire hair surface. The scale is from 0-5, 0 being the hardest and 5 being the easiest.
Airy Foam—a measure of foam density. The scale is from 1-4, 1 being the least airy (small creamy bubbles, shaving cream like) and 4 being the most airy (largest bubbles).
Foam Stability—how well the foam maintains its structure without collapsing. The scale is from 1-4, 1 being the least stable and 4 being the most stable.
Squeaky Clean—a measure of detergency. The scale is from 0-5, 0 being the least clean and 5 being the cleanest.
Ease of Passing Fingers—a measure of conditioning, how tangled hair is after product is rinsed. The scale is from 1-4, 1 being the hardest (most tangled) and 4 being the easiest (least tangled).
Wet Smoothness—another measure of conditioning; this attribute measures the tactile feel of the hair fiber after rinsing the test shampoo. Conditioned fibers are smooth due to the deposition of conditioning agents. Clean, damaged hair feels less smooth and rough. The scale is from 0-5, 0 being the least smooth and 5 being the smoothest.
Coating wet hair—another measure of conditioning, this attribute measures the amount of coating deposited from a shampoo on the hair surface after rinse. The scale is from 0-5, 0 being the least coated and 5 being the most coated.
Shine—this measures the reflection of light off the hair after the product is applied and rinsed and hair is dry. High shine is desirable. The scale is from 1-6, 1 being the least shiny and 6 being the shiniest.
Smooth Hair (feel)—another measure of conditioning, this attributes measures the tactile feel of the fiber after drying the hair. The scale is from 0-5, 0 being the least smooth and 5 being the smoothest.

In this evaluation, a difference of more than 0.5 in any measured property is noticeable.

The results of this assessment are summarized in Table 4 below.

TABLE 4

| Attribute | Example 1 | State of the Art Sulfate Free Moisture Shampoo[1] |
|---|---|---|
| Flash Foam (1st) (0-5) | 2.75 | 2.50 |
| Distribution Ease (0-5) | 2.67 | 2.42 |
| Airy Foam (1st) (1-4) | 2.67 | 2.42 |
| Foam Stability (1st) (1-4) | 3.50 | 3.58 |
| Squeaky Clean (1st) (0-5) | 0.75 | 0.71 |
| Ease of Passing Fingers (1st) (1-4) | 3.08 | 3.00 |
| Wet Smoothness (0-5) | 3.08[2] | 2.58 |
| Coating wet hair (0-5) | 3.00[2] | 2.42 |
| Shine (1-6) | 3.33 | 3.50 |
| Smooth Hair (feel) (0-5) | 2.75 | 2.75 |
| (a)/(b) | 2.3 | 11.4 |

[1] This shampoo contains greater than 20% active surfactants (sulfate free anionic surfactants and amphoteric surfactants), a carbomer, a thickener that is not selected from a hydrophobically-modified acrylic acid based copolymer, and cationic conditioners PQ-10 and PQ-7.
[2] These measurements varied by more than 0.5 from the comparative formula.

As shown in Table 4, the inventive composition of Example 1 has comparable detergency (meaning cleaning power) to the commercial state of the art moisture shampoo. This is accomplished with less total detergent surfactants (15.86%) in contrast to the commercial shampoo which has greater than 20%.

What is claimed is:
1. The present invention relates to an aqueous personal cleansing composition comprising:
(a) from about 3% to about 14%, by weight, of at least one anionic surfactant that is not an alkyl sulfate or alkyl ether sulfate; wherein the anionic surfactant is selected from acyl isethionates, acyl glycinates, acyl taurates, acyl amino acids, acyl sarcosinates, sulfosuccinates, sulfonates, and sulfoacetates and mixtures thereof;
(b) from about 0.5% to about 8%, by weight, of at least one amphoteric surfactant selected from betaines, sultaines, amphoacetates, amphoproprionates, and mixtures thereof;
(c) from about 0.01% to about 2.0%, by weight, of at least one thickener selected from a hydrophobically-modified acrylic acid based copolymer having a molecular weight from about 80,000 to about 2,500,000 grams per mole;
(d) from about 0.01% to about 2%, by weight, of at least one cationic conditioning agent selected from cationic cellulose derivatives, polymer derivatives of diallyldimethyl ammonium chloride, polymer derivatives of methacrylamidopropyltrimethylammonium chloride, amine-functionalized silicones, amino silicones, and mixtures thereof; and (e) at least one nonionic surfactant;

wherein the ratio of the anionic surfactant (a) to the amphoteric surfactant (b) is less than about 9.5, by weight, all weights and ratios being based on the weight percent of each component in the final composition; and wherein the aqueous cleansing composition is sulfate-free.

2. The composition of claim 1 wherein the ratio of the sum of anionic surfactant (a), amphoteric surfactant (b) and nonionic surfactant (e) to viscosity increasing agent (c), by weight, is from about 1 to about 800.

3. The composition of claim 2 wherein the ratio of the at least one anionic surfactant (a) to the at least one amphoteric surfactant (b) is greater than 0.1 and less than 9.5.

4. The composition of claim 3 wherein the ratio of the at least one anionic surfactant (a) to the at least one amphoteric surfactant (b) is from about 1 to about 8.

5. The composition of claim 1 wherein the at least one hydrophobically-modified acrylic acid based polymer thickener (c) is selected from acrylate/$C_{10}$-$C_{30}$ alkyl acrylate copolymers, acrylates/beheneth-25 methacrylate copolymers, carbovynyl polymers, and mixtures thereof.

6. The composition of claim 1 which comprises from about 0.5% to about 2% of at least one non-ionic surfactant (e).

7. The composition of claim 6 wherein the non-ionic surfactant (e) is selected from alkyl polyglucosides, glycol esters, amine oxides, and mixtures thereof.

8. The composition of claim 1 wherein the at least one anionic surfactant (a) is an acyl amino acid selected from sodium cocoyl glycinate, sodium lauroyl sarcosinate and mixtures thereof.

9. The composition of claim 1 wherein at least one anionic surfactant (a) is an isethionate selected from sodium isethionate, sodium lauroyl methyl isethionate, and mixtures thereof.

10. The composition of claim 1 wherein the at least one anionic surfactant (a) is selected from disodium laureth sulfosuccinate, sodium C14-16 olefin sulfonate, sodium lauryl sulfoacetate, and mixtures thereof.

11. The composition of claim 1 wherein at least one amphoteric surfactant (b) is a betaine selected from coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof.

12. The composition of claim 1 wherein the at least one cationic conditioning agent (d) is selected from polyquaternium-7, polyquaternium-10, and amodimethicone, and mixtures thereof.

13. The composition of claim 1 wherein the at least one non-ionic surfactant (e) is selected from decyl glucoside, coco glucoside, PEG-8 glyceryl laurate, polysorbate-40, polyglyceryl-5 laurate, lauramine oxide, and mixtures thereof.

14. An aqueous personal cleansing composition comprising:

(a) from about 5% to about 12%, by weight, of at least one anionic surfactant selected from sodium cocoyl isethionate, sodium lauroyl methyl isethionate, sodium lauroyl sarcosinate, disodium laureth sulfossuccinate, sodium cocoyl glycinate, and mixtures thereof;

(b) from about 1% to about 6%, by weight, of at least one amphoteric surfactant selected from cocamidopropyl betaine, coco-betaine, and mixtures thereof;

(c) from about 0.1% to about 1.0%, by weight, of a thickener selected from acrylates/beheneth-25 methacrylate copolymer;

(d) from about 0.1% to about 1.5%, by weight, of at least one cationic conditioning agent selected from polyquaternium-7, polyquaternium-10, amodimethicone, and mixtures thereof; and (e) from about 0.5% to about 2%, by weight, of at least one nonionic surfactant selected from decyl glucoside, coco glucoside, PEG-8 glyceryl laurate, polysorbate-40, polyglyceryl-5 laurate, lauramine oxide, and mixtures thereof;

wherein the ratio of the anionic surfactant (a) to the amphoteric surfactant (b) is from about 1 to about 8, by weight, all weights and ratios being based on the weight percent of each component in the final composition; and wherein the aqueous cleansing composition is sulfate-free.

15. A method of cleansing a keratinous substrate comprising applying to said substrate an aqueous personal cleansing composition comprising:

(a) from about 3% to about 14%, by weight, of at least one anionic surfactant that is not an alkyl sulfate or alkyl ether sulfate; wherein the anionic surfactant is selected from acyl isethionates, acyl glycinates, acyl taurates, acyl amino acids, acyl sarcosinates, sulfosuccinates, sulfonates, and sulfoacetates;

(b) from about 0.5% to about 8%, by weight, of at least one amphoteric surfactant selected from betaines, sultaines, amphoacetates, amphoproprionates, and mixtures thereof;

(c) from about 0.01% to about 2.0%, by weight, of a thickener selected from a hydrophobically-modified acrylic acid based copolymer having a molecular weight from about 80,000 to about 2,500,000 grams per mole;

(d) from about 0.01% to about 2%, by weight, of at least one cationic conditioning agent selected from cationic cellulose derivatives, polymer derivatives of diallyldimethyl ammonium chloride, polymer derivatives of methacrylamidopropyltrimethylammonium chloride, amine-functionalized silicones, amino silicones, and mixtures thereof; and (e) at least one nonionic surfactant;

wherein the ratio of the anionic surfactant (a) to amphoteric surfactant (b) is from about 1 to about 8, by weight, all weights and ratios being based on the weight percent of each component in the final composition; and wherein the aqueous cleansing composition is sulfate-free.

16. A method of cleansing and conditioning a keratinous substrate comprising applying to said substrate an aqueous personal cleansing composition comprising:

(a) from about 5% to about 12%, by weight, of at least one anionic surfactant that is not an alkyl sulfate or alkyl ether sulfate, the anionic surfactant being selected from acyl isethionates, acyl glycinates, acyl taurates, acyl amino acids, acyl sarcosinates, sulfosuccinates, sulfonates, and sulfoacetates;

(b) from about 1% to about 6%, by weight, of at least one amphoteric surfactant selected from betaines, sultaines, amphoacetates, amphoproprionates, and mixtures thereof;

(c) from about 0.1% to about 1.0%, by weight, of a thickener selected from a hydrophobically-modified acrylic acid based copolymer having a molecular weight from about 80,000 to about 2,500,000 grams per mole;

(d) from about 0.1% to about 1.5%, by weight, of at least one cationic conditioning agent; and (e) at least one nonionic surfactant selected from cationic cellulose derivatives, polymer derivatives of diallyldimethyl ammonium chloride, polymer derivatives of methacrylamidopropyltrimethylammonium chloride, amine-functionalized silicones, amino silicones, and mixtures thereof;

wherein the ratio of the anionic surfactant (a) to amphoteric surfactant (b) is from about 1 to about 8, by weight, all weights and ratios being based on the weight percent of each component in the final composition; and wherein the aqueous cleansing composition is sulfate-free.

17. A process for making an aqueous personal cleansing composition comprising:

(1) contacting:

(a) from about 3% to about 14%, by weight, of at least one anionic surfactant that is not an alkyl sulfate or alkyl ether sulfate; wherein the anionic surfactant is selected from acyl isethionates, acyl glycinates, acyl taurates, acyl amino acids, acyl sarcosinates, sulfosuccinates, sulfonates, and sulfoacetates;

(b) from about 0.5% to about 8%, by weight, of at least one amphoteric surfactant selected from betaines, sultaines, amphoacetates, amphoproprionates, and mixtures thereof;

(c) from about 0.01% to about 2.0%, by weight, of a thickener selected from a hydrophobically-modified acrylic acid based copolymer having a molecular weight from about 80,000 to about 2,500,000 grams per mole;

(d) from about 0.01% to about 2%, by weight, of at least one cationic conditioning agent selected from cationic cellulose derivatives, polymer derivatives of diallyldimethyl ammonium chloride, polymer derivatives of methacrylamidopropyltrimethylammonium chloride, amine-functionalized silicones, amino silicones, and mixtures thereof; and (e) from about 0.5% to about 2% least one nonionic surfactant;

wherein the ratio of the anionic surfactant (a) to the amphoteric surfactant (b) is from about 1 to about 8, by weight, all weights and ratios being based on the weight percent of each component in the final composition; and wherein the aqueous cleansing composition is sulfate-free; and (2) mixing until the composition is uniform.

* * * * *